(12) United States Patent
Friedman et al.

(10) Patent No.: US 6,423,010 B1
(45) Date of Patent: Jul. 23, 2002

(54) OSCILLOMETRIC BLOOD PRESSURE MONITOR WITH IMPROVED PERFORMANCE IN THE PRESENCE OF ARRHYTHMIAS

(75) Inventors: Bruce Friedman; Lawrence T. Hersh, both of Tampa; Christopher J. Dedyo, Lutz, all of FL (US)

(73) Assignee: Critikon Company, L.L.C., Tampa, FL (US)

( * ) Notice: Subject to any disclaimer, the term of this patent is extended or adjusted under 35 U.S.C. 154(b) by 26 days.

(21) Appl. No.: 09/678,650

(22) Filed: Oct. 4, 2000

(51) Int. Cl.[7] .................................................. A61B 5/02
(52) U.S. Cl. ........................ 600/494; 600/493; 600/495
(58) Field of Search .............................. 600/493–496, 600/490

(56) References Cited

U.S. PATENT DOCUMENTS

| | | | |
|---|---|---|---|
| 4,262,674 A | | 4/1981 | Uemura et al. |
| 4,349,034 A | * | 9/1982 | Ramsey, III ................ 600/494 |
| 4,360,029 A | | 11/1982 | Ramsey, III |
| 5,014,714 A | | 5/1991 | Millay et al. |
| 5,238,001 A | | 8/1993 | Gallant et al. |
| 5,404,878 A | * | 4/1995 | Frankenreiter et al. ...... 600/493 |
| 5,651,370 A | * | 7/1997 | Hersh et al. ................. 600/494 |
| 5,800,359 A | * | 9/1998 | Medero et al. .............. 600/454 |
| 5,865,756 A | | 2/1999 | Peel, III |
| 5,931,790 A | | 8/1999 | Peel, III |
| 6,050,951 A | * | 4/2000 | Friedman et al. ........... 600/485 |

FOREIGN PATENT DOCUMENTS

EP   0 960 598 A1   5/1998
EP   0 898 935 A1   8/1998

* cited by examiner

*Primary Examiner*—Kevin Shaver
*Assistant Examiner*—Patricia Mallari
(74) *Attorney, Agent, or Firm*—Larry L. Saret; Michael Best & Friedrich LLC (57) ABSTRACT

The present invention relates to an improved apparatus and method for measuring blood pressure. Both include a first sensor for detecting an instantaneous pulse rate, an inflatable cuff, and a second sensor to monitoring the pressure within the cuff. The cuff sensor adapted to detect oscillometric complexes associated with a patient's pulse. Both the apparatus and the method provide for detecting arrhythmia from the patient's instantaneous pulse rate. A characteristic of the oscillometric complexes is measured, and match determination means provided for determining whether at least two adjacent oscillometric complexes are equivalent. A first set matching criteria are used under normal conditions. A second set of matching criteria are used when arrhythmia are detected. A controller is provided for controlling the pressure within the cuff. At the outset of a blood pressure measurement the cuff is inflated to a pressure greater than the patient's systolic pressure. In response to a determination that two adjacent oscillometric complexes are equivalent the control means reduces the cuff pressure by a fixed increment and the match determination means continues to determine whether adjacent complexes are equivalent. A blood pressure determination means is provided responsive to the control means and the measuring means. The blood pressure determination means compares the measured characteristic of the oscillometric complexes from various cuff pressures and determines the cuff pressure at which the measured characteristic reaches a limit. This cuff pressure corresponds to the patient's mean arterial pressure.

34 Claims, 5 Drawing Sheets

OSCILLOMETRIC BLOOD PRESSURE MONITOR WITH IMPROVED PERFORMANCE IN THE PRESENCE OF ARRHYTHMIAS

BACKGROUND OF THE INVENTION

The present invention relates to a blood pressure monitoring device which employs the oscillometric method of determining blood pressure, and a method for improving the performance of such a device in the presence of arrhythmias.

The basis for the oscillometric method of measuring blood pressure is disclosed in U.S. Pat. Nos. 4,349,034 and 4,360,029 both to Ramsey, III the disclosures of which are incorporated herein by reference. Using the technique disclosed by Ramsey, III the oscillometric method of measuring blood pressure involves applying an inflatable cuff around an extremity of a patient's body, such as the a patient's upper arm. The cuff is then inflated to a pressure above the patient's systolic pressure and then incrementally reduced in a series of small steps. A pressure sensor measures the cuff pressure at each step. The sensitivity of the sensor is such that pressure fluctuations within the artery resulting from the beats of the patient's pulse may be detected. These pulses are transferred to the inflated cuff causing slight pressure variations within the cuff which are detected by the pressure sensor. The pressure sensor produces an electrical signal which typically comprises a DC component representing the incremental cuff pressure and a series of small periodic variations associated with the beats of the patient's pulse. These small variations are often referred to as "oscillation complexes" or simply "oscillations".

A patient's blood pressure may be estimated based on an analysis of these oscillation complexes. After filtering out the DC component and amplifying the signal generated by the cuff pressure sensor, peak pulse amplitudes (PPA) may be determined for each oscillometric complex. The PPA will tend to increase as the cuff pressure is reduced until a peak amplitude is reached. Once this peak has been reached, the PPA will begin to decrease with further reductions in cuff pressure. The peak pulse amplitudes thus form an oscillometric blood pressure envelope for the patient. The cuff pressure at which the oscillations have a maximum value has been found to be representative of the patient's mean arterial pressure (MAP). The systolic and diastolic pressures can be derived either as predetermined fractions of MAP, or by more sophisticated estimating techniques using direct processing of the oscillation complexes.

Figure 1:
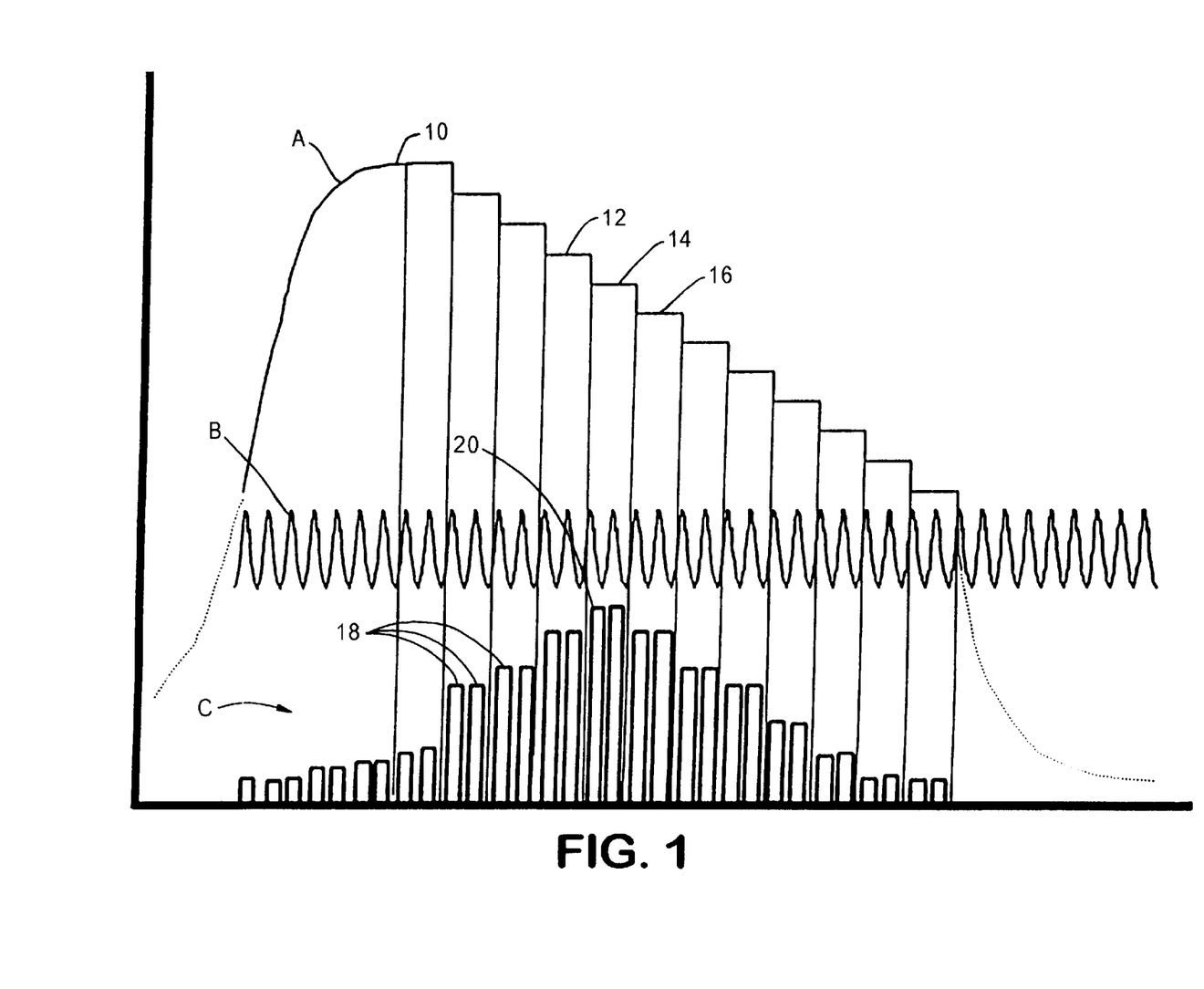
FIG. 1 is a graph showing various waveforms taken from an oscillometric blood pressure measurement.

FIG. 1 shows the basic elements of measuring a patient's blood pressure using the oscillometric method. Three waveforms are shown. Curve A represents the overall cuff pressure of the inflatable cuff, curve B represents an invasive arterial waveform showing the periodic pressure variations corresponding to the patient's pulse, and curve C represents the measured peak pulse amplitudes for the oscillometric complexes associated with each pulse of waveform B. As can be seen, the cuff is first inflated to a maximum pressure 10, and then reduced in a series of small incremental steps such as steps 12, 14, and 16. Oscillations 18 corresponding to each pulse of the arterial waveform B are measured at each incremental cuff pressure. The PPA of the oscillations increases with each decrement of cuff pressure until the PPA reach a maximum at cuff pressure 14. The PPA are diminished with every subsequent reduction in cuff pressure. Thus, the cuff pressure at step 14 represents the patient's mean arterial pressure, and the patient's systolic and diastolic pressures can be determined therefrom.

A problem with this method of measuring blood pressure is that blood pressure measurements can be skewed due to artifacts caused by patient motion or by the presence of arrhythmias. Events such as these can adversely affect the peak pulse amplitudes detected by the cuff's pressure sensor, resulting in erroneous blood pressure measurements. The Ramsey, III patents listed above disclose a first technique for rejecting artifacts. There, a plurality of oscillometric complexes are measured at each incremental cuff pressure. Selected parameters such as peak height and time rate of change of successive complexes, and series of complexes are evaluated relative to specific artifact discrimination criteria. Complexes which do not fall within the predefined criteria are rejected and are not used in forming the blood pressure measurement. Thus, as shown in FIG. 1, two matched oscillation complexes are measured at each cuff pressure before the cuff pressure is reduced to the next step. This technique works well to reject artifacts due to motion, but it can unduly lengthen the procedure for obtaining a blood pressure measurement in the presence of arrhythmias. In fact, in some cases it can prevent a measurement from being completed.

Figure 2:
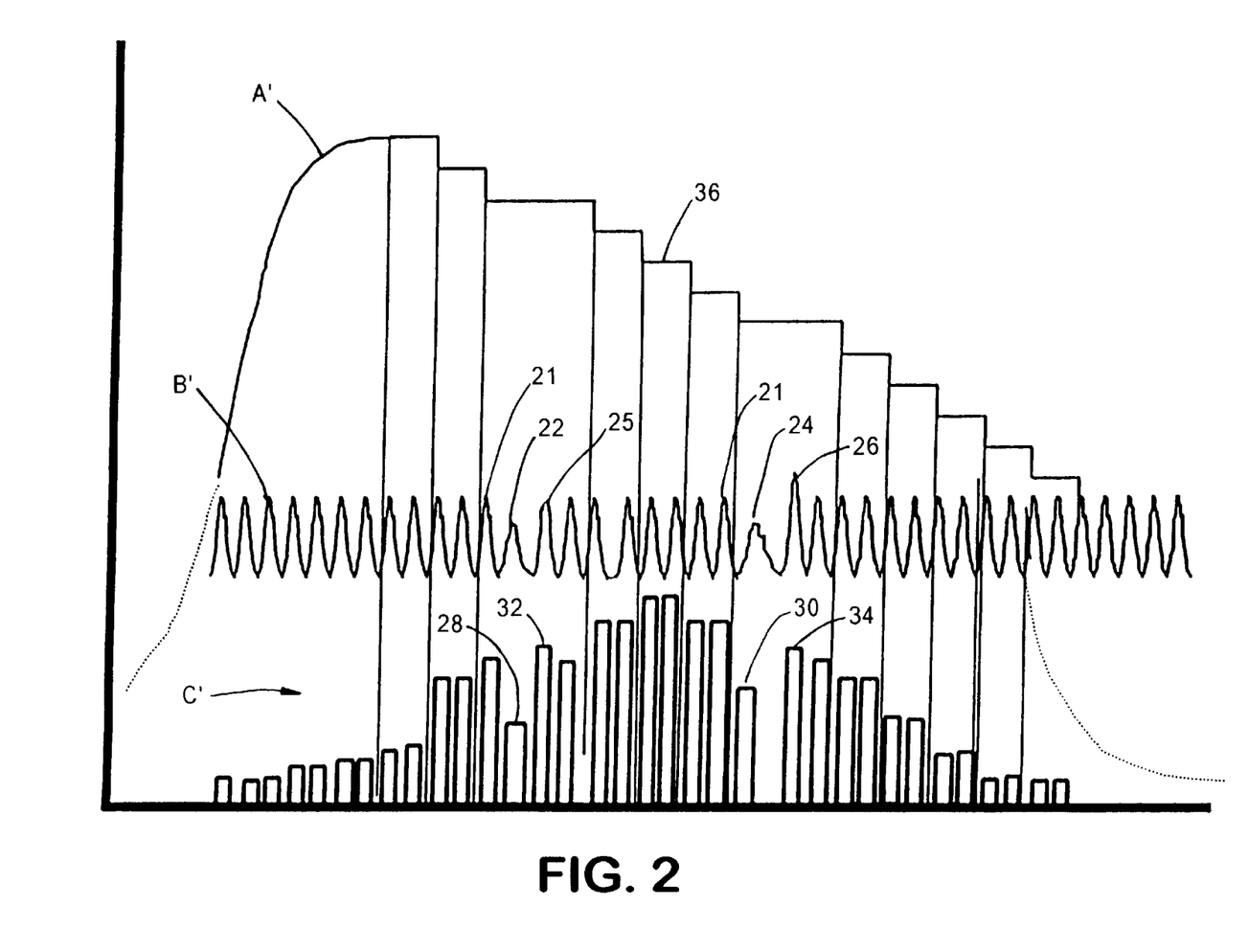
FIG. 2 is a graph showing various waveforms taken from an oscillometric blood pressure measurement when arrhythmias are present.

FIG. 2 shows how the presence of an arrhythmia affects blood pressure measurements using the oscillometric method. The three curves A', B' and C' are identical to those of FIG. 1 except for the presence of non-sinus beats 22, 24 which are best seen on the invasive arterial waveform B'. Non-sinus beats 22, 24 occur prematurely. Therefore, the period between the preceding sinus beats 21, 23 and the non-sinus beats 22, 24 will be shorter than the normal period between sinus beats, and the period between the non-sinus beats 22, 24 and the immediately following sinus beats 25, 26 will be extended. Furthermore, because the non-sinus beats 22, 24 occur prematurely, a smaller amount of blood is pumped from the heart than would otherwise be the case and the arterial pressure associated with the non-sinus beats is reduced. As can be seen in FIG. 2, the PPA measured from the oscillations 28, 30 associated with the non-sinus beats 22, 24 are subsequently reduced. Likewise, because the time between the non-sinus beats 22, 24 and the next following sinus beats 25, 26 is extended, beats 25, 26 pump a greater amount of blood than normal sinus beats and the pulse pressure is increased as reflected in the higher than normal PPA of oscillations 32, 34 associated with beats 25, 26 following non-sinus beats 22, 24. Thus, using the method for rejecting artifacts disclosed by Ramsey, III at cuff pressure increments 36 and 37 no two adjacent oscillometric complexes have the same PPA. Thus, if the matching criteria for determining matching oscillation complexes are drawn toward a narrow range of peak-pulse amplitude variations no match would be found at pressure steps 36 and 37.

A number of other references disclose using various methods for detecting the presence of arrhythmias and rejecting the oscillometric complexes associated with irregular heart beats. For example, European Patent No. EP 0895748 to Sohma et al. discloses a blood pressure monitoring device which uses an ECG and a pulse sensor to measure pulse transit time (PTT). Changes in PTT from sample to sample as well as changes in PPA are used to detect the presence of arrhythmias. However, Sohma et al. do not utilize this information to alter the function of a non-invasive blood pressure monitor. Similarly, European Patent 960598 to Forstner discloses an NIBP monitor which uses variances in pulse period to detect arrhythmias. Variations in the pulse period are used to reject those oscillometric complexes associated with arrhythmias or to send a signal indicating the presence of an arrhythmia.

U.S. Pat. No. 5,404,878 to Frankenreiter discloses a method and apparatus to measure and sort oscillations by amplitude and period and reject those that fall outside predefined limits.

U.S. Pat. No. 5,865,756 discloses an NIBP which uses an ECG to detect arrhythmias and a pulse oximeter to measure blood volume. This apparatus corrects the amplitude of oscillometric complexes which are "corrupted" by the presence of arrhythmias. The pulse volume measurement is used to correct the size of the oscillations so that the complexes may be used in calculating blood pressure.

The prior art recognizes the problems associated with calculating blood pressure in the presence of artifacts and arrhythmias. In attempts to deal with these problems, however, the prior art does not disclose a satisfactory method for rejecting artifacts while compensating for the presence of arrhythmias and calculating an accurate blood pressure measurement in a timely manner when arrhythmias are present. Therefore, a need exists for an NIBP monitor capable of rejecting artifacts and accurately measuring blood pressure in the presence of non-sinus (irregular) heartbeats. Ideally, such an NIBP monitor should reject oscillometric complexes resulting from artifacts but should be able to compensate for and include oscillometric complexes resulting from non-sinus beats in calculating blood pressure. In this manner, the time for carrying out a blood pressure measurement will be reduced. It is also desirable to provide an NIBP monitor capable of providing a blood pressure reading based only on sinus beats and another blood pressure reading based only on non-sinus beats such that both a sinus and nonsinus blood pressure readings may be displayed, or the average of the two readings may be displayed.

SUMMARY OF THE INVENTION

A first aspect of the invention is an improved non-invasive blood pressure (NIBP) monitor having improved artifact rejection characteristics and improved performance in the presence of arrhythmia. The NIBP monitor of the present invention includes a first sensor for detecting an instantaneous pulse rate, an inflatable cuff, and a second sensor adapted to monitor the pressure within the cuff. In addition to measuring the overall pressure within the cuff, the pressure sensor is adapted to detect oscillometric complexes associated with a patient's pulse when the cuff is inflated around one of the patient's limbs. The NIBP monitor further includes arrhythmia detection means for detecting the presence of arrhythmias from the instantaneous pulse rate. Typically this will comprise a signal processor capable of identifying arrhythmia and other irregular features of an ECG signal or other signal related to the patient's pulse. A signal processor may further provide means for measuring a characteristic of the oscillometric complexes detected by the cuff sensor. The blood pressure monitor further comprises match determination means for determining whether at least two adjacent oscillometric complexes associated with adjacent cardiac pulses are equivalent based on matching criteria related to the measured characteristic of the oscillometric complexes. The match determination means employs a second set of matching criteria when the arrhythmia detection means determines that one of the oscillometric complexes being compared is associated with an arrhythmia and employs a first set of matching criteria otherwise. A pressure controller is provided for controlling the pressure within the cuff. At the outset of a blood pressure measurement the cuff is inflated to a pressure greater than the patient's systolic pressure. The pressure controller responds to the match determination means such that in response to a determination that two adjacent oscillometric complexes are equivalent the control means reduces the cuff pressure by a fixed increment, whereupon the match determination means continues to determine whether adjacent complexes are equivalent at the new cuff pressure. Lastly, the NIBP monitor includes means for determining the patient's blood pressure responsive to the pressure controller and the measuring means. The blood pressure determination means compares the measured characteristic of the oscillometric complexes obtained at the various incremental cuff pressures and determines the cuff pressure at which the measured characteristic reaches a limit, for example, when the pulse peak amplitude reaches a maximum. The cuff pressure at which the measured characteristic reaches such a limit corresponds to the patient's mean arterial pressure (MAP) and is displayed by the monitor. The systolic and diastolic pressures may be derived from the MAP and also displayed.

According to this first aspect of the invention, the first sensor may comprise an ECG monitor, a blood volume sensor, both an ECG monitor and a blood volume sensor, or some other sensor from which information regarding the patient's heart rhythm may be obtained. The first and second sets of matching criteria employed by the match determination means may comprise first and second amplitude variation thresholds or first and second period variation thresholds, a combination of amplitude and period variation thresholds, or some other measurable characteristic of the oscillometric complexes. When amplitude variation thresholds are employed oscillometric complexes are considered equivalent when they have amplitudes that vary by an amount less than the amplitude variation threshold. When period variation thresholds are employed oscillometric complexes are considered equivalent when the difference between a first period measured between a first oscillometric complex and the immediately preceding complex and the time period measured between a second oscillometric complex and the immediately preceding first oscillometric complex differs by an amount less than the period variation threshold. In an embodiment of the invention the first amplitude variation threshold comprises 12% and the second amplitude variations threshold comprises 24%. In another embodiment of the invention, a first period variation threshold comprises 25% and a second period variation threshold comprises 50%.

A second aspect of the present invention relates to an improved method for measuring a patient's blood pressure. The improved method comprises the steps of applying an inflatable cuff around an extremity of the patient. The cuff is then inflated to a cuff pressure above the patient's systolic blood pressure. A sensor within the inflated cuff detects oscillation complexes within said cuff resulting from each beat of the patient's pulse. The next step involves measuring a characteristic of the oscillation complexes, such as, for example, the peak pulse amplitude (PPA) of the oscillation complexes. The method further includes the step of establishing first and second sets of matching criteria related to the characteristic measured for each oscillometric complex. The first and second sets of matching criteria are used for determining whether adjacent complexes are equivalent. A second sensor is to be provided to detect the presence of arrhythmias. Adjacent oscillometric complexes are then compared with one another to determine whether the complexes are equivalent. The first set of matching criteria is used to determine equivalence when an arrhythmia has not been detected and the second set of matching criteria is employed when an arrhythmia has been detected. Upon detecting equivalent adjacent complexes, the cuff pressure is reduced by a predetermined increment and oscillation complexes are again detected by the sensor within the inflatable cuff. Again, a characteristic of the oscillation complexes is measured and the measured characteristics of adjacent oscillometric complexes are compared to determine whether any two adjacent complexes are equivalent. This process is repeated until it is determined that the measured characteristic of the oscillometric complexes at a given cuff pressure has reached a maximum relative to the measured characteristic of two adjacent equivalent complexes measured at other cuff pressures. The cuff pressure at which the measured characteristic reaches a maximum corresponds to the patient's mean arterial pressure. According to this method of the invention, the second sensor for detecting arrhythmias may be an ECG monitor, a pulse oximeter, both an ECG and a pulse oximeter, or some other sensor.

Further, the step of establishing first and second sets of matching criteria may comprise establishing a first amplitude variation threshold such that oscillometric complexes having amplitudes differing by an amount less than the first amplitude variation threshold are considered equivalent according to the first set of matching criteria. This step may also comprise establishing a second amplitude variation threshold such that oscillometric complexes having amplitudes that differ by an amount less than the second amplitude variation threshold are considered equivalent according to the second set of matching criteria. The first amplitude variation threshold may comprise a difference in amplitude no greater than 12%, and the second amplitude variation threshold may comprise a difference in amplitude of no greater than 24%.

Alternatively, the step of establishing first and second sets of matching criteria may comprise establishing first and second period variation thresholds such that when the period between a first oscillometric complex and an immediately preceding oscillometric complex and the period between a second oscillometric complex and the first oscillometric complex varies by an amount less than the first period variation threshold, the first and second oscillometric complexes are considered equivalent according to the first set of matching criteria. When the period between the first oscillometric complex and the immediately preceding oscillometric complex and the period between a second oscillometric complex and the first oscillometric complex varies by an amount less than the second period variation threshold, the first and second oscillometric complexes are considered equivalent according to the second set of matching criteria. The first period variation threshold may comprise a difference in period of no greater than 25%, and the second period variation threshold may comprise a difference in period of no greater than 50%.

Finally, according to this second aspect of the invention, the first and second sets of matching criteria may comprise a combination of an amplitude variation threshold, period variation threshold, or some other measurable feature of the oscillometric complexes.

DETAILED DESCRIPTION OF THE PREFERRED EMBODIMENTS

Figure 3:
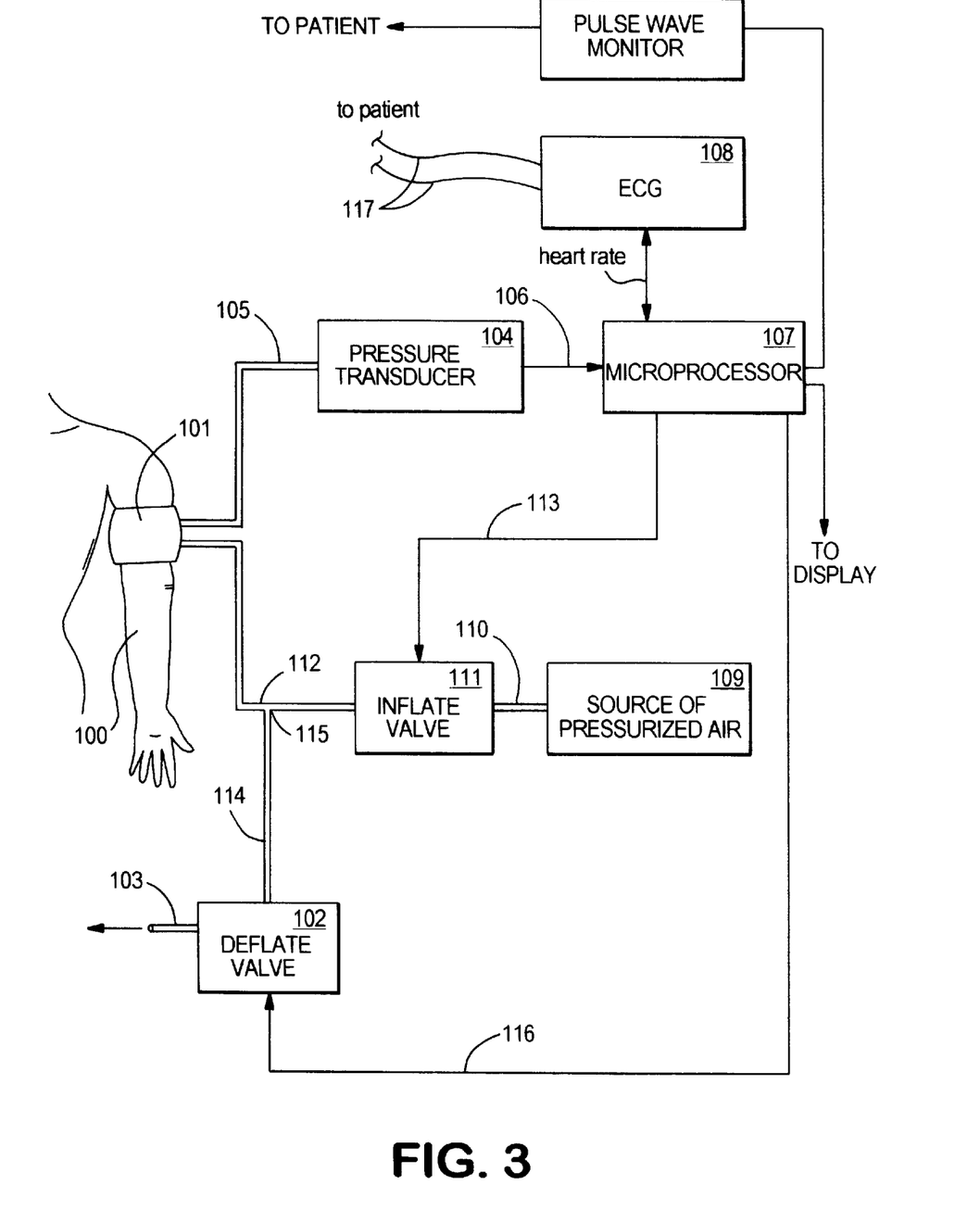
FIG. 3 is a functional block diagram of a blood pressure monitor according to the present invention.

A functional block diagram of an improved non-invasive blood pressure (NIBP) monitoring system 100 is shown in FIG. 3. The non-invasive blood pressure monitoring system includes an inflatable cuff 101 adapted to be inflated around a portion of a patient's body, such as around the patient's arm 100. An inflate valve 111 and a deflate valve 102 are operatively connected to the cuff to control the air pressure within the cuff. A first air duct 110 connects the inflate valve to a source of pressurized air 109, and a second air duct 112 connects the inflate valve to the cuff. Another air duct 114 forms a "T" with air duct 112 at 115, connecting the deflate valve 102 to the cuff 101 as well. A short exhaust duct 103 provides an outlet from the cuff to the atmosphere through the deflate valve 102. A pressure transducer 104 is provided which communicates with the interior of the cuff 101 via air duct 105. Pressure transducer 104 is thus arranged to sense the air pressure within cuff 101. An ECG 108 is provided having leads 117 connected to sensors attached to the patient's body as is known in the art. A pulse oximeter 122 is also attached to the patient and sends a signal to a pulse wave monitor 120 via pulse oximeter lead 123. Finally, a microprocessor 107 is provided to control the air pressure within the cuff 101 and to receive and interpret data from the pressure transducer 104, the ECG monitor 108, and the pulse wave monitor 120.

Figure 4:
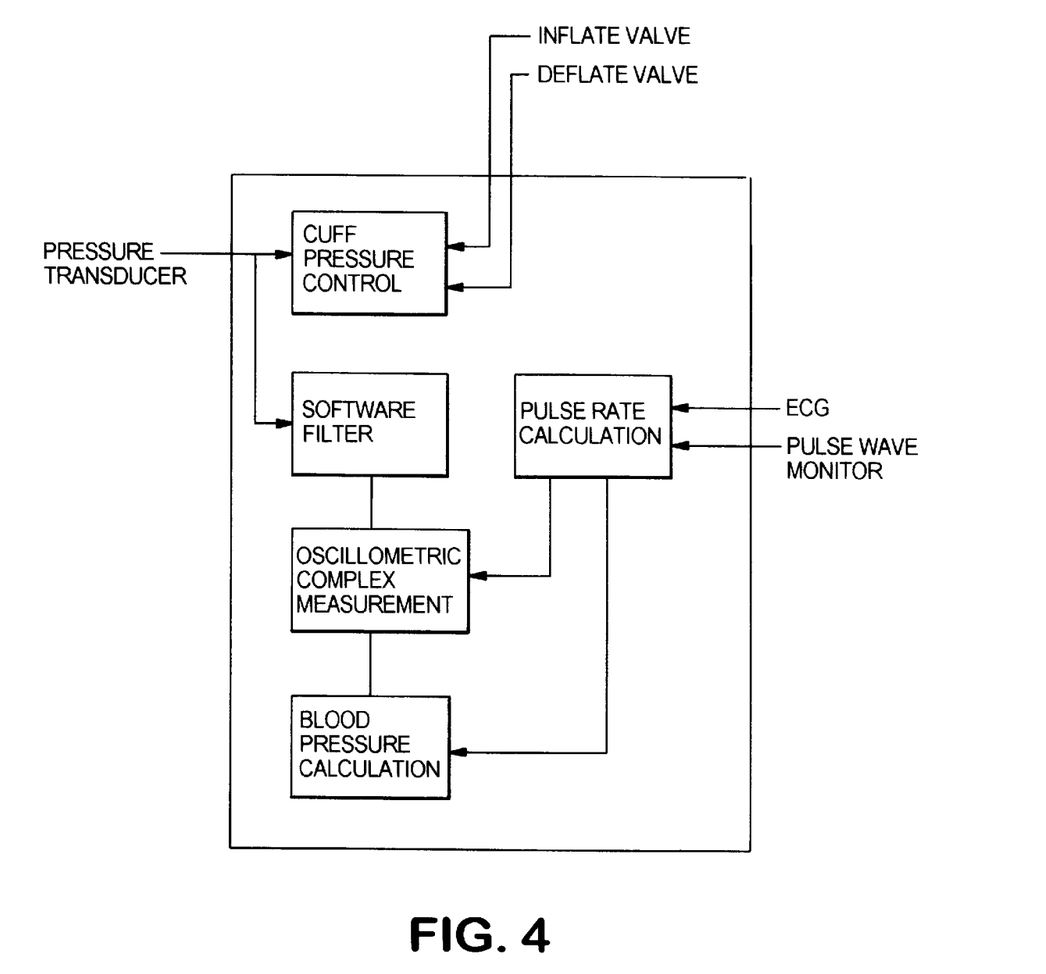
FIG. 4 is a functional block diagram of the software components for implementing a blood pressure monitor according to the present invention.
Figure 5:
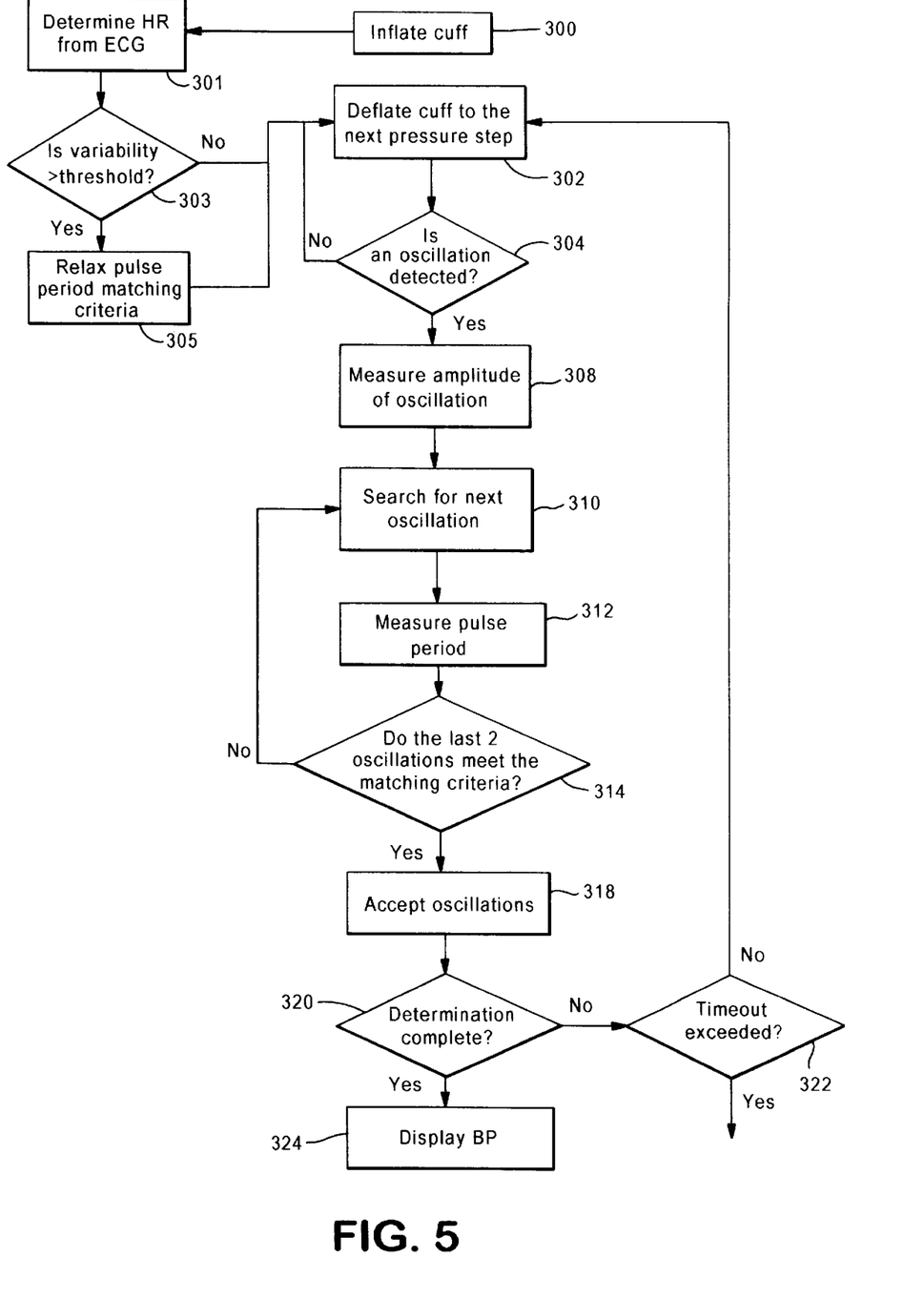
FIG. 5 is a flow chart describing a method for measuring blood pressure according to the present invention.

The microprocessor receives pressure data from the pressure transducer 104 over input line 106, and heart rate information from the ECG monitor over input line 118, and pulse amplitude data from the pulse wave monitor 121 over input line 121. Output line 113 connects the microprocessor 107 to the inflate valve 111, and output line 116 connects the microprocessor 107 to the deflate valve 102. A functional block diagram of the software components of the operating software for microprocessor 107 is shown in FIG. 4. The functional block includes cuff pressure controller 124, software filter 125, oscillometric complex measurement 126, pulse rate calculation 127 and a blood pressure calculation 128.

In operation the cuff pressure control 124 receives input from the pressure transducer 104, and controls the inflate valve 111 and deflate valve 102 to maintain a desired pressure within the inflatable cuff 101. In accordance with the oscillometric method of measuring blood pressure, upon initiation of a blood pressure measurement the cuff pressure control 124 closes the exhaust valve 102 and opens the inflate valve 111 to allow pressurized air to flow from the pressurized air source into the cuff 101. The pressure controller 124 monitors the output from the pressure transducer 104 and closes the inflate valve 111 when the pressure within the cuff exceeds the patient's systolic blood pressure. Thereafter, the cuff pressure controller reduces the cuff pressure in a series of incremental steps by selectively opening and closing the exhaust valve 102, periodically venting excess air within the cuff to atmosphere.

In addition to sensing the overall cuff pressure, the pressure transducer 104 senses oscillometric complexes superimposed on the overall cuff pressure signal. The signal from pressure transducer 104 will comprise a DC component representing the static pressure of the inflated cuff 102 at the particular pressure increment at which the measurement is taken, plus a variable component added to the DC signal. These variable components are known as oscillation complexes which result from variations in the cuff pressure caused by the patient's pulse. The pressure transducer signal is input to the software filter 125. The software filter 125 removes the DC component of the transducer signal and amplifies the remaining variable signal. This signal is then provided to the oscillometric complex measurement and comparison function 126. This function measures various characteristics of the filtered oscillometric waveform. For example, the oscillometric complex measuring and comparison function may measure the peak amplitude of the oscillation complex signal and/or the time period between the oscillation complexes.

Once the various characteristics of oscillometric waveform have been measured, the oscillometric complex measurement and comparison function 126 compares the measured characteristic from adjacent oscillometric complexes to determine whether the adjacent oscillometric complexes are equivalent. If the measured characteristics of two adjacent oscillometric complexes differ by an amount greater than a predetermined value, the two oscillometric complexes are deemed to be not equivalent. However, if the difference between the measured characteristics falls within the predefined range, the two oscillometric complexes will be judged equivalent.

When the NIBP monitor is taking a blood pressure measurement the cuff pressure control 124 responds to a signal from the oscillometric complex measurement function 126. The cuff pressure control 124 maintains the cuff pressure at a given pressure increment until the oscillometric complex measurement function 126 determines that two consecutive oscillometric complexes are equivalent or until a time-out occurs. When the oscillometric complex measurement function 126 determines that two consecutive oscillometric complexes are equivalent, the cuff pressure control 124 reduces the cuff pressure to the next increment. If a time-out occurs before two consecutive oscillometric complexes are detected, the blood pressure measurement is halted.

The blood pressure calculation function block 128 receives the values of the measured characteristics of the equivalent oscillometric complexes from the oscillometric complex measurement and comparison function 126 as well as the cuff pressures at which they were obtained from the cuff pressure control 124. The patient's mean arterial blood pressure is calculated by comparing the measured characteristic of equivalent adjacent oscillometric complexes detected at each of the different cuff pressures at which the oscillometric complexes were measured. Referring back to FIG. 1, and as described in the background section of the specification, the measured characteristics of the oscillometric complexes will increase with each decrement in cuff pressure until the measured characteristic reaches a maximum. Thereafter, the measured characteristic will begin to decrease with each subsequent cuff pressure. The cuff pressure at which the measured characteristic reaches a maximum represents the patient's mean arterial blood pressure (MAP). The systolic and diastolic pressures may be calculated from the MAP according to methods which are known in the art. The calculated MAP, systolic, and diastolic pressures may then be displayed on a display.

As has been noted, the measured characteristic of oscillometric complexes resulting from artifacts and from non-sinus beats will generally not be consistent with the characteristics measured from oscillometric complexes associated with sinus beats. Artifacts are effectively rejected by waiting to receive two adjacent equivalent complexes before proceeding to the next cuff pressure increment. However, frequently occurring arrhythmias may unacceptably extend the time required to receive two adjacent equivalent complexes. In order to avoid unacceptably prolonging the blood pressure measurement and avoid a potential time out, the pulse rate calculating function 127 monitors the signals from one or both of the pulse wave monitor 120 and the ECG monitor 108. An output from the pulse rate calculation function 127 alerts the oscillometric complex measurement and comparison function 126 of the presence of an arrhythmia so that the oscillometric measurement and function 126 comparison function 126 can adjust accordingly. The oscillometric complex measurement and function adjusts to the presence of an arrhythmia by lowering the threshold for determining equivalence between adjacent oscillometric complexes. For example, if the measured characteristic of the oscillometric complexes being compared is the peak pulse amplitude (PPA), under normal conditions the oscillation complex measurement and comparison function 126 may consider two oscillation complexes equivalent if the difference in their PPA is less than 5%. If it has been determined that one of the oscillometric complexes being compared is the result of a non-sinus beat, however, the equivalence threshold may be reduced to 10%. With the lower threshold, two oscillometric complexes may be considered equivalent even though their PPAs differ by an amount that is greater than would otherwise be acceptable. The result is that two equivalent oscillometric pulses may be detected much sooner than would otherwise be the case, and the blood pressure measurement may proceed to the next incremental cuff pressure.

Turning to FIG. 4, an improved method for measuring blood pressure according to the present invention is provided. The method involves applying an inflatable cuff around a patient's extremity and applying at least one sensor from which the patient's heart rate may be determined. The sensor may be an ECG monitor, pulse oximeter, or some other type of sensor. The method begins at step 300 where the cuff is inflated around a portion of the patient's body. At step 301 the heart rate is determined. At decision block 303 it is determined whether or not the variability of the heart rate is greater than a predetermined variability threshold. If not, the method proceeds to step 302. However, if the heart rate variability exceeds the predetermined variability threshold, pulse matching criteria for determining whether oscillometric pulses are equivalent are relaxed prior to proceeding to step 302. At step 302 the cuff pressure is reduced by a set amount. The method then proceeds to decision block 304 where oscillation complexes are to be detected. If no oscillations are detected the process control returns to step 302 where the cuff pressure is again reduced by the same set amount. If an oscillation is detected at step 304 the amplitude of the oscillation is measured at step 308. Thereafter, at step 310, the method calls for detecting the next oscillation and measuring the period between oscillations. At step 314 it is determined whether the oscillations meet the matching criteria. If not, the method returns to step 310 and again searches for the next oscillation complex and determines whether it matches the previous oscillation complex according to the match criteria. When it is determined at step 314 that two adjacent oscillations meet the matching criteria, the oscillations are accepted at step 318 and the method moves on to decision block 320 where it is determined whether the blood pressure measurement is complete.

This decision is based on the measured amplitude of the presently accepted oscillations as well as the accepted oscillations obtained at previous cuff pressures. If it is determined that the peak amplitude of the oscillations has already been reached, then the determination is complete, and the blood pressure corresponding to the cuff pressure at which the maximum oscillation peak amplitude was recorded is displayed. If it is determined at block 320 that the maximum oscillation peak amplitude has not been reached, the method checks whether a measurement time out has occurred. If yes, the blood pressure measurement is halted. If not, the method returns to step 302 and the cuff pressure is again reduced by the same set amount, and the steps 304–320 are repeated until either a time-out occurs or the blood pressure determination is complete.

In an alternate embodiment of the invention, a method is provided for measuring blood pressure in the presence of bi-geminey type arrhythmia. With this type of arrhythmia, sinus and non-sinus beats are present in approximately equal numbers. Non-sinus beats alternate with sinus beats in a regular pattern. The oscillation complexes associated with the non-sinus beats will vary significantly from the complexes associated with sinus beats. However, the oscillometric complexes associated with non-sinus beats will exhibit a strong resemblance one to another, as will the complexes associated with sinus beats. Because the blood pressure wave associated with non-sinus beats is significantly different from that of sinus beats, it is difficult to get a true reading of blood pressure. In this embodiment of the invention two separate blood pressure readings are made. One blood pressure reading corresponds to the blood pressure associated with sinus beats, and the other reading corresponds to the blood pressure associated with non-sinus beats. Once the two blood pressure readings are made, each can be displayed separately or an average of the two can be displayed.

It should be noted that various changes and modifications to the present invention may be made by those of ordinary skill in the art without departing from the It should be noted that various changes and modifications to the present invention may be made by those of ordinary skill in the art without departing from the spirit and scope of the present invention which is set out in the attached claims. Furthermore, those of ordinary skill in the art will appreciate that the foregoing description is by way of example only, and is not intended to be limiting of the invention as described in the appended claims.

What is claimed is:

1. A method for measuring a patient's blood pressure comprising the steps of:
    applying an inflatable cuff around an extremity of said patient;
    inflating said cuff to a pressure above said patient's systolic blood pressure;
    detecting oscillation complexes within said cuff;
    measuring a characteristic of said oscillation complexes;
    establishing first and second sets of matching criteria based on said measured characteristic of said oscillation complexes for determining whether adjacent oscillation complexes are equivalent;
    providing a sensor to detect the presence of arrhythmias;
    comparing adjacent complexes to determine whether said oscillation complexes are equivalent according to said first set of matching criteria when an arrhythmia has not been detected and according to said second set of matching criteria when an arrhythmia has been detected;
    upon detecting equivalent adjacent complexes, deflating said cuff pressure by a predetermined increment and again detecting oscillation complexes within said cuff, measuring said characteristic of said oscillation complexes, and comparing said characteristic of adjacent oscillation complexes to determine whether any two adjacent oscillation complexes are equivalent;
    repeating the preceding step until it is determined that the measured characteristic of two equivalent adjacent oscillation complexes at a given cuff pressure has reached a maximum relative to the measured characteristic of the two adjacent equivalent oscillation complexes measured at other cuff pressures, the given cuff pressure at which said measured characteristic reaches a maximum corresponding to the patient's mean arterial pressure.

2. The method of claim 1 wherein the step of providing a second sensor comprises providing an ECG monitor.

3. The method of claim 1 wherein the step of providing a second sensor comprises providing a blood volume sensor.

4. The method of claim 3 wherein said blood volume sensor comprises a blood oximeter.

5. The method of claim 3 wherein the step of providing a second sensor further comprises providing an ECG monitor.

6. The method of claim 1 wherein the step of establishing first and second sets of matching criteria comprises establishing a first peak pulse amplitude variation threshold such that oscillometric complexes having peak pulse amplitudes that differ by an amount less than said first amplitude variation threshold are considered equivalent according to said first set of matching criteria.

7. The method of claim 6 wherein said first amplitude variation threshold comprises 12%.

8. The method of claim 6 wherein the step of establishing first and second sets of matching criteria further comprises establishing a second amplitude variation threshold such that oscillometric complexes having amplitudes that differ by an amount less than said second amplitude variation threshold are considered equivalent according to said second set of matching criteria.

9. The method of claim 8 wherein said second amplitude variation threshold comprises 24%.

10. The method of claim 1 wherein the step of establishing first and second sets of matching criteria comprises establishing a first period variation threshold such that when the period between a first oscillometric complex and an immediately preceding oscillometric complex and the period between a second oscillometric complex and the first oscillometric complex differ by an amount less than said first period variation threshold said oscillometric complexes are considered equivalent according to said first set of matching criteria.

11. The method of claim 10 wherein said first period variation threshold comprises 25%.

12. The method of claim 10 wherein the step of establishing first and second sets of matching criteria further comprises establishing a second period variation threshold such that when the period between a first oscillometric complex and an immediately preceding oscillometric complex and the period between a second oscillometric complex and the first oscillometric complex differ by an amount less than said second period variation threshold said oscillometric complexes are considered equivalent according to said second set of matching criteria.

13. The method of claim 12 wherein said second period variation threshold comprises 50%.

14. The method of claim 1 wherein the step of establishing first and second sets of matching criteria further comprises establishing a first amplitude variation threshold and a first period variation threshold such that first and second oscillometric complexes having amplitudes that differ by an amount less than said first amplitude variation threshold and the period between the first oscillometric complex and an immediately preceding oscillometric complex and the period between the second oscillometric complex and the first oscillometric complex differ by an amount less than said first period variation threshold, the first and second oscillometric complexes are considered equivalent according to the first set of matching criteria.

15. The method of claim 1 wherein the step of establishing first and second sets of matching criteria further comprises establishing a second amplitude variation threshold and a second period variation threshold such that first and second oscillometric complexes having amplitudes that differ by an amount less than said second amplitude variation threshold and the period between the first oscillometric complex and an immediately preceding oscillometric complex and the period between the second oscillometric complex and the first oscillometric complex differ by an amount less than said second period variation threshold, the first and second oscillometric complexes are considered equivalent according to the second set of matching criteria.

16. An apparatus for measuring blood pressure comprising:
a first sensor for detecting an instantaneous pulse rate;
an inflatable cuff;
a second sensor associated with the inflatable cuff configured to monitor the pressure within said cuff, including detecting oscillometric complexes associated with a patient's pulse when said cuff is inflated around an extremity of said patient;
arrhythmia detection means for detecting the presence of arrhythmias from said instantaneous pulse rate;
measuring means for measuring a characteristic of said oscillometric complexes;
match determination means for determining whether at least two adjacent oscillometric complexes associated with adjacent cardiac pulses are equivalent based on matching criteria related to said measured characteristic, said match determination means employing a second set of matching criteria when said arrhythmia detection means determines that at least one of the oscillometric complexes being compared is associated with an arrhythmia, and employing a first set of matching criteria otherwise;
control means for controlling the pressure within said cuff responsive to said match determination means such that, at the outset of a blood pressure measurement, said cuff is inflated to a pressure greater than the patient's systolic pressure, in response to a determination that two adjacent oscillometric complexes are equivalent, said control means reducing the cuff pressure by a fixed increment, whereupon said match determination means continues to determine whether adjacent complexes are equivalent; and
blood pressure determination means responsive to said control means and said measuring means, said blood pressure determination means comparing the measured characteristic of the oscillometric complexes obtained at the various incremental cuff pressures and determining the cuff pressure at which said measured characteristic reaches a limit, said cuff pressure at which said measured characteristic reaches said limit corresponding to the patient's mean arterial pressure.

17. The apparatus of claim 16 wherein said first sensor comprises an ECG monitor.

18. The apparatus of claim 16 wherein the first sensor comprises a blood volume sensor.

19. The apparatus of claim 18 wherein said blood volume sensor comprises a pulse oximeter.

20. The apparatus of claim 18 wherein the first sensor further comprises an ECG monitor.

21. The apparatus of claim 16 wherein first and second sets of matching criteria comprise first and second amplitude variation thresholds such that oscillometric complexes having amplitudes that differ by an amount less than said first amplitude variation threshold are considered equivalent according to said first set of matching criteria, and oscillometric complexes having amplitudes that differ by an amount less than said second amplitude variation threshold are considered equivalent according to said second set of matching criteria.

22. The method of claim 21 wherein said first amplitude variation threshold comprises 12%.

23. The apparatus of claim 22 wherein said second amplitude variation threshold comprises 24%.

24. The apparatus of claim 16 wherein the first and second sets of matching criteria comprise first and second period variation thresholds such that when the period between a first oscillometric complex and an immediately preceding oscillometric complex and the period between a second oscillometric complex and the first oscillometric complex differ by an amount less than said first period variation threshold said oscillometric complexes are considered equivalent according to said first set of matching criteria, and when the period between the first oscillometric complex and the immediately preceding oscillometric complex and the period between the second oscillometric complex and the first oscillometric complex differ by an amount less than said second period variation threshold, said oscillometric complexes are considered equivalent according to said second set of matching criteria.

25. The apparatus of claim 24 wherein said first period variation threshold comprises 25%.

26. The apparatus of claim 25 wherein said second period variation threshold comprises 50%.

27. The apparatus of claim 16 wherein the first set of matching criteria comprises a first amplitude variation threshold and a first period variation threshold such that first and second oscillometric complexes having amplitudes that differ by an amount less than said first amplitude variation threshold and the period between the first oscillometric complex and an immediately preceding oscillometric complex and the period between the second oscillometric complex and the first oscillometric complex differ by an amount less than said first period variation threshold, the first and second oscillometric complexes are considered equivalent according to the first set of matching criteria, and the second set of matching criteria comprises a second amplitude variation threshold and a second period variation threshold such that first and second oscillometric complexes having amplitudes that differ by an amount less than said second amplitude variation threshold and the period between the first oscillometric complex and an immediately preceding oscillometric complex and the period between the second oscillometric complex and the first oscillometric complex differ by an amount less than said second period variation threshold, the first and second oscillometric complexes are considered equivalent according to the second set of matching criteria.

28. A method of rejecting artifacts and compensating for non-sinus beats when performing an oscillometric blood pressure measurement using an inflatable cuff whereby oscillometric complexes are detected at a plurality of incremental cuff pressures, the method of rejecting artifacts comprising the steps of:

provinding a first sensor for monitoring a patient's sinus rhythm and detecting non-sinus beats;

providing a second sensor for detecting oscillometric complexes associated with each beat of the patient's pulse;

measuring a characteristic of said oscillation complexes at each incremental cuff pressure;

comparing said characteristic measured from oscillation complexes associated with adjacent pulses to determine whether said oscillometric complexes are equivalent based on specific matching criteria;

proceeding to the next incremental cuff pressure when it has been determined that two adjacent oscillometric complexes are equivalent; and relaxing the matching criteria when comparing the measured characteristic of oscillometric complexes obtained when non-sinus beats are detected.

29. The method of claim 28 wherein the step of providing a first sensor comprises providing an ECG monitor.

30. The method of claim 28 wherein the step of providing a first sensor comprises providing a blood volume sensor.

31. The method of claim 30 wherein said blood volume sensor comprises a pulse oximeter.

32. The method of claim 28 wherein the step of comparing a characteristic of said oscillation complexes comprises comparing the amplitude of said oscillation complexes.

33. The method of claim 32 wherein the step of relaxing the matching criteria comprises allowing oscillation complexes having greater amplitude variations to be considered equivalent.

34. The method of claim 32 wherein the step of relaxing the matching criteria comprises considering oscillation complexes having greater variance in the period between adjacent complexes to be considered equivalent.

* * * * *